(12) United States Patent
Weaver et al.

(10) Patent No.: US 11,540,962 B2
(45) Date of Patent: Jan. 3, 2023

(54) PRODUCT BAG RETENTION ASSEMBLY

(71) Applicant: Donna Weaver, Chicago, IL (US)

(72) Inventors: Donna Weaver, Chicago, IL (US);
Daniel G. Meiser, Wilder, KY (US)

(73) Assignee: Donna Weaver, Chicago, IL (US)

( * ) Notice: Subject to any disclaimer, the term of this patent is extended or adjusted under 35 U.S.C. 154(b) by 914 days.

(21) Appl. No.: 16/193,989

(22) Filed: Nov. 16, 2018

(65) Prior Publication Data

US 2020/0155394 A1 May 21, 2020

(51) Int. Cl.
*A61G 7/05* (2006.01)
*A61F 5/44* (2006.01)
*B65F 1/14* (2006.01)

(52) U.S. Cl.
CPC .......... *A61G 7/0503* (2013.01); *A61F 5/4404* (2013.01); *B65F 1/1415* (2013.01); *A61F 5/44* (2013.01); *A61G 7/05* (2013.01); *A61M 2209/082* (2013.01)

(58) Field of Classification Search
CPC ..... A61F 5/44; A61F 5/445; A61M 2209/082; A61M 5/1415; A61M 1/69; A61G 7/0503; A61G 2203/80; A61G 7/05; B65F 1/1426; B65F 2210/18; B65F 1/1415; B65D 2590/046
See application file for complete search history.

(56) References Cited

U.S. PATENT DOCUMENTS

| | | | |
|---|---|---|---|
| 1,876,230 A * | 9/1932 | Horner | A61G 7/0503 5/308 |
| 2,557,674 A | 6/1951 | McRae | |
| 2,784,423 A * | 3/1957 | Droeger | A61G 7/0503 5/503.1 |
| 2,886,036 A * | 5/1959 | Price | A61F 5/44 604/326 |
| 2,999,387 A * | 9/1961 | Andelin | B65D 75/5877 D24/118 |
| 3,180,384 A * | 4/1965 | Seifert | B60N 3/08 383/23 |
| 3,220,434 A | 11/1965 | Garth | |
| 3,231,901 A | 2/1966 | Kennedy | |
| 3,254,817 A | 6/1966 | Bartz | |
| 3,345,023 A * | 10/1967 | Scott | A61G 7/0503 248/95 |
| 3,371,897 A * | 3/1968 | Serany, Jr. | A61G 7/0503 248/95 |

(Continued)

OTHER PUBLICATIONS

European Patent Application No. 19209317.7, Extended European Search Report, dated Jul. 1, 2020.

(Continued)

*Primary Examiner* — Jonathan Liu
*Assistant Examiner* — Taylor Morris
(74) *Attorney, Agent, or Firm* — Marshall, Gerstein & Borun LLP (57) ABSTRACT

A product bag suspension assembly includes a rod having a first end, a second end, and a body extending between the first end and the second end. A platform is operatively coupled to the second end of the rod and defines an aperture arrangement configured to receive a mounting device of a product bag. The rod is configured to suspend the product bag in an upright position when the product bag is coupled to the platform.

13 Claims, 6 Drawing Sheets

(56) References Cited

U.S. PATENT DOCUMENTS

| | | | | |
|---|---|---|---|---|
| 3,471,871 A * | 10/1969 | Nociti | A61F 5/44 | 4/484 |
| 3,534,738 A * | 10/1970 | Huck | A61G 7/0503 | 604/325 |
| 3,537,109 A * | 11/1970 | Spurrier | A61F 5/44 | 4/144.1 |
| 3,548,827 A * | 12/1970 | Abel | A61G 7/0503 | 604/318 |
| 3,716,055 A * | 2/1973 | Schultze | A61G 7/0503 | 604/325 |
| 3,809,577 A * | 5/1974 | Thorsson et al. | A61L 11/00 | 134/42 |
| 3,865,165 A * | 2/1975 | Glass | A61G 7/0503 | 604/322 |
| 4,027,842 A * | 6/1977 | Mittleman | A61F 5/44 | 248/75 |
| 4,178,934 A * | 12/1979 | Forman | A61F 5/44 | 24/54 |
| 4,194,715 A * | 3/1980 | Forman | A61F 5/44 | 248/311.2 |
| 4,219,177 A * | 8/1980 | O'Day | A61G 7/0503 | 248/215 |
| 4,235,350 A * | 11/1980 | Valentino | A61G 7/0503 | 206/806 |
| 4,254,771 A * | 3/1981 | Vidal | A61F 5/441 | 604/325 |
| RE30,607 E * | 5/1981 | Manschot | A61B 5/20 | 600/575 |
| 4,305,405 A * | 12/1981 | Meisch | A61B 5/20 | 53/157 |
| 4,312,352 A * | 1/1982 | Meisch | A61G 7/0503 | 604/322 |
| 4,317,550 A * | 3/1982 | Hannah | A61M 5/1415 | 248/95 |
| 4,326,521 A * | 4/1982 | Marsan | A61F 5/445 | 604/342 |
| 4,332,252 A * | 6/1982 | Taylor | A61G 7/0503 | 128/DIG. 24 |
| 4,393,880 A * | 7/1983 | Taylor | A61G 7/0503 | 248/95 |
| 4,496,354 A * | 1/1985 | Steer | A61F 5/44 | 206/466 |
| 4,501,584 A * | 2/1985 | Cianci | A61G 7/0503 | 248/95 |
| 4,534,766 A * | 8/1985 | Steer | A61M 1/69 | 604/323 |
| 4,562,984 A | 1/1986 | Sherlock et al. | | |
| 4,579,126 A * | 4/1986 | Cianci | A61F 5/4404 | 600/580 |
| 4,606,736 A * | 8/1986 | Van De Weghe | A61F 5/44 | 604/322 |
| 4,650,478 A * | 3/1987 | Dunn | A61M 1/69 | 604/322 |
| 4,673,401 A * | 6/1987 | Jensen | A61F 5/453 | 604/353 |
| 4,731,062 A * | 3/1988 | Gross | A61B 5/20 | 600/575 |
| 4,773,768 A | 9/1988 | Leeper | | |
| 4,787,584 A | 11/1988 | Palmer | | |
| 4,850,375 A * | 7/1989 | Rosenberg | B65B 69/0016 | 600/580 |
| 4,874,387 A * | 10/1989 | Boone | A61F 5/44 | 604/326 |
| 4,946,451 A * | 8/1990 | Cianci | A61F 5/4404 | 604/350 |
| 4,988,062 A * | 1/1991 | London | A61G 7/0503 | 128/DIG. 26 |
| 5,119,675 A * | 6/1992 | Mohiuddin | A61B 5/20 | 600/580 |
| 5,282,599 A * | 2/1994 | Arpaia | A47K 11/12 | 211/88.01 |
| 5,349,710 A | 9/1994 | Dunn | | |
| 5,375,799 A | 12/1994 | Rhodes | | |
| 5,382,244 A * | 1/1995 | Telang | A61M 1/61 | 604/319 |
| 5,393,113 A * | 2/1995 | Walsh | A45F 5/10 | 294/170 |
| 5,423,782 A | 6/1995 | Wolrich | | |
| 5,472,167 A * | 12/1995 | Shillington | A47F 5/0853 | 211/94.01 |
| 5,489,281 A * | 2/1996 | Watanabe | A61M 1/882 | 604/326 |
| 5,527,007 A * | 6/1996 | Weilbacher | A61G 7/0503 | 248/304 |
| 5,651,152 A * | 7/1997 | Ritchie | A47C 21/00 | 294/143 |
| 5,829,723 A * | 11/1998 | Brunner | A61M 5/1413 | 248/222.13 |
| 5,836,553 A * | 11/1998 | Bergaila | B65F 1/1415 | 248/101 |
| 5,938,646 A | 8/1999 | Carter | | |
| 6,109,460 A * | 8/2000 | Herlevi | A61B 50/20 | 211/106 |
| 6,129,684 A * | 10/2000 | Sippel | A61B 5/208 | 600/575 |
| 6,423,041 B1 * | 7/2002 | Grant | A61G 7/0503 | 141/313 |
| 6,637,938 B2 * | 10/2003 | Watkins | D06F 95/004 | 383/33 |
| 6,675,998 B2 * | 1/2004 | Forsman | B65D 75/5866 | 220/705 |
| 7,014,077 B2 * | 3/2006 | Brown | A45F 3/20 | 220/375 |
| 7,090,179 B2 | 8/2006 | DiMaggio | | |
| 7,398,951 B1 * | 7/2008 | Sugalski | A61G 7/0503 | 248/214 |
| 7,462,171 B2 * | 12/2008 | Salvadori | A61F 5/4404 | 604/317 |
| 7,703,723 B1 * | 4/2010 | Cooper | B65B 67/1233 | 248/97 |
| 7,814,590 B2 | 10/2010 | Powell et al. | | |
| 8,109,914 B2 * | 2/2012 | Garrett | A61G 7/0503 | 604/326 |
| 8,177,097 B2 * | 5/2012 | Duran | A45F 3/20 | 222/105 |
| 8,267,358 B1 | 9/2012 | Letson | | |
| 8,430,855 B2 * | 4/2013 | Burgess | A61F 5/44 | 604/317 |
| 8,672,402 B1 * | 3/2014 | Arnold | B60R 7/043 | 297/188.2 |
| 9,072,637 B1 * | 7/2015 | Puri | A61J 1/16 | |
| 9,095,222 B2 * | 8/2015 | Asaf | A61G 7/0522 | |
| 2001/0011166 A1 * | 8/2001 | Harper | A61M 1/70 | 604/322 |
| 2005/0087660 A1 * | 4/2005 | Want | A61M 5/1414 | 248/304 |
| 2006/0011784 A1 * | 1/2006 | Liebermann | A61G 7/0503 | 248/95 |
| 2007/0057134 A1 * | 3/2007 | Cheng | A61G 7/0503 | 248/311.2 |
| 2007/0107130 A1 * | 5/2007 | Elhabashy | A61B 50/20 | 5/622 |
| 2007/0203463 A1 * | 8/2007 | Salvadori | A61F 5/4404 | 604/323 |
| 2007/0215782 A1 * | 9/2007 | Phung | A61M 1/61 | 248/691 |
| 2008/0319406 A1 | 12/2008 | Garrett | | |
| 2009/0030384 A1 * | 1/2009 | Christen | A61G 7/0503 | 604/319 |
| 2009/0216206 A1 * | 8/2009 | Nishtala | A61F 5/4405 | 604/327 |
| 2011/0128152 A1 * | 6/2011 | Bregeon | A61M 5/16845 | 340/603 |
| 2012/0216348 A1 * | 8/2012 | Cox | A61G 7/018 | 5/421 |
| 2013/0094786 A1 | 4/2013 | Zyburt et al. | | |
| 2013/0161350 A1 * | 6/2013 | Murrieta | A61J 15/0011 | 222/105 |

(56) References Cited

U.S. PATENT DOCUMENTS

| | | |
|---|---|---|
| 2016/0324708 A1* | 11/2016 | Ellis .................... A61G 7/0507 |
| 2017/0020711 A1 | 1/2017 | Nishtala et al. |
| 2017/0121104 A1* | 5/2017 | Degnan ................ B65F 1/1415 |
| 2017/0281836 A1* | 10/2017 | Giezendanner ..... A61M 1/0001 |
| 2018/0049909 A1 | 2/2018 | Johnson |
| 2018/0245967 A1* | 8/2018 | Parker ................... G01G 23/18 |
| 2019/0358075 A1* | 11/2019 | Scharich, III ........ A61G 7/0503 |
| 2020/0030191 A1* | 1/2020 | Santillan ................ F16B 2/185 |
| 2020/0306421 A1* | 10/2020 | Christensen ............ A61M 1/69 |
| 2021/0080054 A1* | 3/2021 | Jackson ............. A61M 5/1415 |
| 2021/0138135 A1* | 5/2021 | Fini .................... A61M 1/1656 |

OTHER PUBLICATIONS

European Patent Application No. 19209317, Partial European Search Report, dated Mar. 31, 2020.

* cited by examiner

PRODUCT BAG RETENTION ASSEMBLY

FIELD OF DISCLOSURE

The present disclosure is directed to an assembly for holding a product bag, and in particular, to an assembly for holding a product bag in an upright position.

BACKGROUND

A number of different medical conditions may require a patient to temporarily or permanently wear an ostomy bag or a catheter collection bag to collect waste. For example, an ostomy bag is a medical product bag that is fluidly connected to an ostomy, which is a port made in a patient's abdomen to permit stool or urine to leave the patient's body. When the patient is active, for example, during the day, the patient wears an ostomy bag underneath their clothing and empties the ostomy bag as needed. When the patient is inactive, for example, at night, the patient can connect their ostomy bag to a night-time drainage bag to collect overflow of the ostomy bag while the patient is asleep.

SUMMARY

In a first exemplary aspect, a product bag retention assembly may include a brace having a first end and a second end defining a hook. A handle may include a grip portion and a support portion extending from the grip portion. The grip portion may be removably coupled to the hook of the brace, and the support portion may have a first surface and a second surface. A platform may be operatively coupled to the support portion of the handle and may extend away from the first surface of the support portion. The platform may define an aperture sized to receive a mounting device of a product bag. The assembly may further include a bag including a wall defining a chamber to receive the product bag. The bag may include a hole formed in the wall and sized to receive the platform. Optionally, a ring may be removably coupled to the platform. A portion of the bag may be clamped between the ring and the platform when the platform is disposed through the hole of the bag and the ring is coupled to the platform.

In a second exemplary aspect, a product bag retention assembly may include a brace having a first end, a second end, and a body extending between the first end and the second end. A platform may be operatively coupled to the second end of the brace. The platform may define an aperture arrangement configured to receive a mounting device of a product bag. The brace may be configured to suspend the product bag in an upright position when the product bag is coupled to the platform.

In a third exemplary aspect, a method for suspending a product bag from a piece of furniture may include providing a rod having a first end, a second end, and a body extending between the first end and the second end. The second end may be operatively coupled to a platform for receiving a mounting device of a product bag. The method may include disposing the first end of the rod between a first surface and a second surface of a piece of furniture such that the second end of the rod is spaced away from the piece of furniture. Further, the method may include coupling a product bag to the platform such that the product bag is suspended outwardly and away from the piece of furniture and hangs from the platform in an upright position.

In further accordance with any one or more of the foregoing first, second, and third aspects, a product bag retention assembly and/or a method of suspending a product bag may further include any one or more of the following preferred forms.

In a preferred form, the platform may be integrally formed with the handle.

In a preferred form, when the hook is coupled to the grip portion of the handle, the brace may suspend the bag in an upright position.

In a preferred form, when the ring is coupled to the platform, the ring may clamp a portion of the bag against the support portion of the handle.

In a preferred form, the platform may define a plurality of apertures arranged to receive and support a mounting device of a product bag.

In a preferred form, the platform may have an oval-shaped perimeter and the ring may have an oval-shaped opening sized to receive the perimeter of the platform.

In a preferred form, a latch may be formed in the platform and may be configured to elastically deform to allow the ring to snap fit to the platform.

In a preferred form, a notch may be formed in the grip portion of the handle.

In a preferred form, the notch may be sized to receive the hook of the brace.

In a preferred form, the platform may include a hook adjacent to the second surface of the support portion.

In a preferred form, the hook of the platform may be removably coupled to a second hole of the bag.

In a preferred form, the aperture arrangement may define a first aperture, a second aperture, a first slot, a second slot, and a third slot.

In a preferred form, the first, second, and third slots may be disposed between the first and second apertures.

In a preferred form, a handle may include a grip portion and a support portion extending from the grip portion.

In a preferred form, the grip portion may be removably coupled to the second end of the brace and the platform may be coupled to the support portion.

In a preferred form, the platform may be operatively coupled to the brace by way of the support portion of the handle.

In a preferred form, the second end of the brace may define a hook arranged to couple to the grip portion of the handle.

In a preferred form, the platform may be integrally formed with the second end of the rod.

In a preferred form, a bag may include a wall having a hole extending through the wall and sized to receive the platform.

In a preferred form, the bag may define a chamber sized to receive the product bag.

In a preferred form, the brace may be configured to suspend the product bag in an upright position when the platform extends through the hole in the bag and is coupled to the platform.

In a preferred form, a ring may be removably coupled to the platform to secure the bag to the platform.

In a preferred form, the platform may have an oval-shaped perimeter and the ring may have an oval-shaped opening sized to receive the perimeter of the platform.

In a preferred form, the platform may include a guide plate perpendicular relative to the platform.

In a preferred form, the platform may extend away from the first surface of the support portion a first distance and may extend away from the second surface of the support portion a second distance greater than the first distance.

In a preferred form, the guide plate may define a slot sized to slidably receive a portion of a mounting device of a product bag.

In a preferred form, a peg may extend from the platform and may be configured to securably engage the ring.

In a preferred form, the brace may be a rod and the first end of the rod may be bent.

In a preferred form, the rod may include a ridge extending between the first end and the second end.

In a preferred form, the platform may have an oval-shaped perimeter.

In a preferred form, the platform may extend in a perpendicular direction relative to the support portion.

In a preferred form, the platform may extend away from the second surface of the support portion.

In a preferred form, the support portion may include a base plate stepped relative to the grip portion.

In a preferred form, the base plate may define the first surface and the second surface of the support portion.

In a preferred form, a product bag may include a mounting arm attached to a wall of the product bag.

In a preferred form, the aperture of the platform may be sized to receive a portion of the mounting device of the product bag.

In a preferred form, the aperture arrangement may include a plurality of apertures.

In a preferred form, the handle may be coupled to the hook of the brace by a snap-fit connection.

In a preferred form, the ring may be removably attached to an exterior surface of the bag wall when the ring is coupled to the platform.

In a preferred form, the platform may be symmetrical about a centerline.

In a preferred form, coupling a product bag to the platform may include sliding a mounting device of the product bag through an aperture formed in the platform.

In a preferred form, the method may include coupling a handle to a hook formed in the second end of the rod.

In a preferred form, the handle may include a grip portion and a support portion extending from the grip portion.

In a preferred form, the platform may extend outwardly from the support portion of the handle.

In a preferred form, the method may include coupling a bag to the platform by disposing a portion of the platform through a hole in the bag.

In a preferred form, the bag may include a wall defining a chamber sized to receive the product bag. The hole may be formed in the wall of the bag.

In a preferred form of the method, coupling the handle to the hook may include snap-fitting the hook into a notch formed in the grip portion of the handle.

In a preferred form, the method may include securably attaching a ring to the platform such that a portion of the bag is clamped between the ring and the platform.

In a preferred form, the method may include coupling a second bag to the platform by disposing a portion of the platform through a hole in the second bag.

In a preferred form, the method may include removing the ring from the platform and removing the bag from the platform.

In a preferred form, the method may include attaching the ring to the platform to clamp a portion of the second bag between the ring and the platform.

Any one or more of these aspects may be considered separately and/or combined with each other in any functionally appropriate manner. In addition, any one or more of these aspects may further include and/or be implemented in any one or more of the optional exemplary arrangements and/or features described hereinafter. These and other aspects, arrangements, features, and/or technical effects will become apparent upon detailed inspection of the figures and the following description.

DETAILED DESCRIPTION

Figure 1:
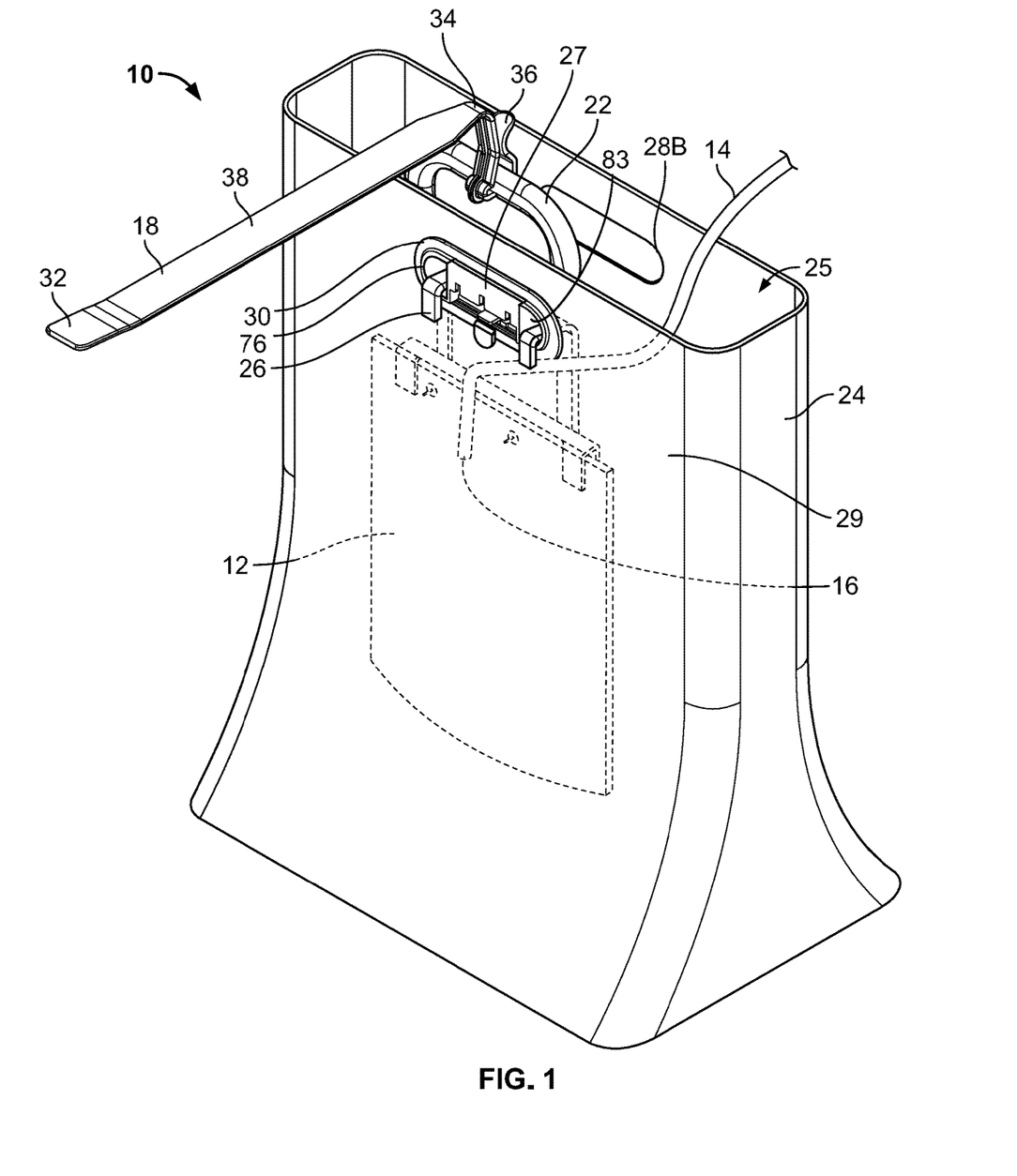
FIG. 1 is a perspective view of a first exemplary product bag retention assembly in accordance with the teachings of the present disclosure.
Figure 2:
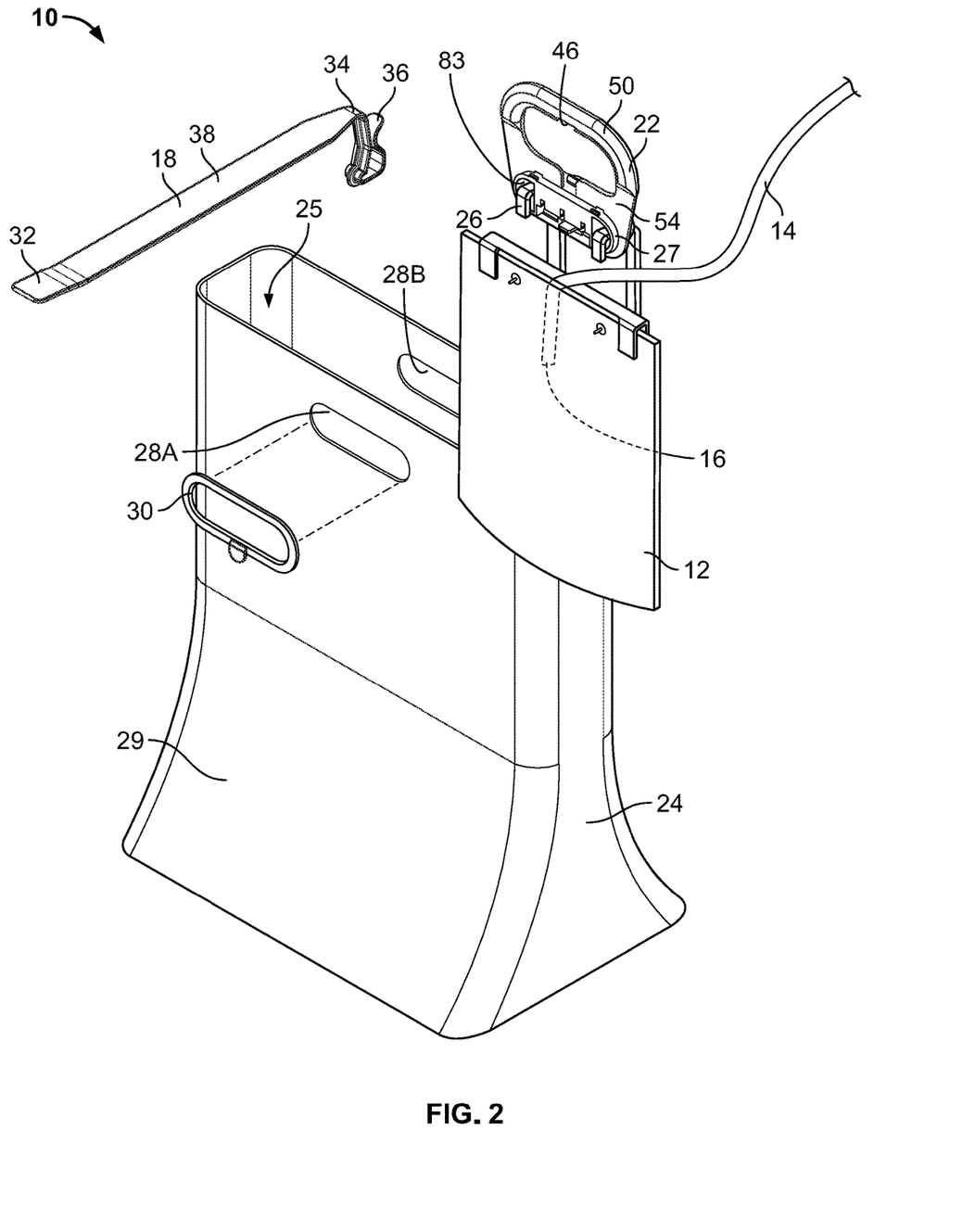
FIG. 2 is an exploded perspective view of the product bag retention assembly of FIG. 1.

In FIGS. 1 and 2, a first exemplary product bag retention assembly 10 safeguards against leakage of a product bag 12, such as a night-time drainage bag that is attached to a patient or to a drainage bag connected to the patient via a tube 14. For example, the product bag 12 may be used by an ostomy patient such that a first end (not shown) of the tube 14 is connected to the ostomy patient's ostomy bag via the tube 14 to collect fluids, and a second end 16 of the tube 14 is in fluid communication with an interior chamber of the product bag 12. In another example, the product bag 12 may be used by a catheter patient and is connected to the catheter patient's drainage bag via the tube 14. The assembly 10 of FIG. 1 includes a support brace 18, a handle 22 coupled to the brace 18, and a security bag 24 coupled to the handle 22 and supportive of the product bag 12. A mounting device 26 (e.g., first and second mounting arms) of the product bag 12 is attached to the handle 22 of the assembly 10 to hang the product bag 12 from the handle 22. As shown in FIG. 1, the handle 22 is partially disposed within the bag 24 such that the product bag 12 is suspended within a chamber 25 defined by a wall 29 of the bag 24. The bag 24 is a reusable and/or disposable bag that is sized to surround the product bag 12 and catch any fluid leaking from the product bag 12 (e.g., through a loose valve or leaking tube). A platform 27 of the handle 22 is disposed within a handle defined by a hole 28A (FIG. 2) formed in the wall 29 of the bag 24, and, optionally, a ring 30 is removably coupled to the handle 22 to clamp the bag 24 between the ring 30 and the handle 22. The brace 18, which is a rod 18, may be inserted between two surfaces of a piece of furniture, for example, between a box spring and a mattress of a typical bed, to securely suspend the product bag 12 in an upright position, above the ground, and away from the piece of furniture. When the product bag 12 is attached to the assembly 10, the product bag 12 is kept out of the way from the patient, is discreetly suspended with the security bag 24 from a bedside or other piece of furniture, and remains connected to the patient to collect an overflow of fluid while the patient rests.

Some examples may be described using the expression "coupled" and "connected" along with their derivatives. For example, some examples may be described using the term "coupled" to indicate that two or more elements are in direct physical contact. The term "coupled," however, may also mean that two or more elements are not in direct contact with each other, but yet still co-operate or interact with each other. The disclosed examples are not limited in this context.

As shown in FIG. 2, the product bag 12 may be coupled to the handle 22 before attaching the handle 22 to the security bag 24 or to the rod 18. In this way, the product bag 12 can hang directly from the handle 22 and can be used separately from the assembly 10 (i.e., without using the rod 18 or the bag 24) to transport the product bag 12. For example, by removing the handle 22 from the rod 18, a patient may carry the product bag 12 to the bathroom to empty and rinse the product bag 12 before using the product bag 12 again. The rod 18 remains attached to a piece of furniture so that the patient can easily connect the handle 22 to the rod 18 for use.

The security bag 24 of the illustrated example may prop against a ground surface or may be spaced away from the ground surface when suspended from the rod 18. The security bag 24 includes first and second holes 28A, 28B, however, in other examples, the holes 28A, 28B may instead be slits formed in the wall 29 of the bag 24. In yet another example, the security bag 24 may not have any holes, but is instead capable of being trapped between the ring 30 and the handle 22 and/or cut to form holes to accommodate the platform 27. Further, the security bag 24 is made of a plastic material that is leak-proof and durable to hold a product bag 12 full of fluid without breaking or leaking.

Figure 3:
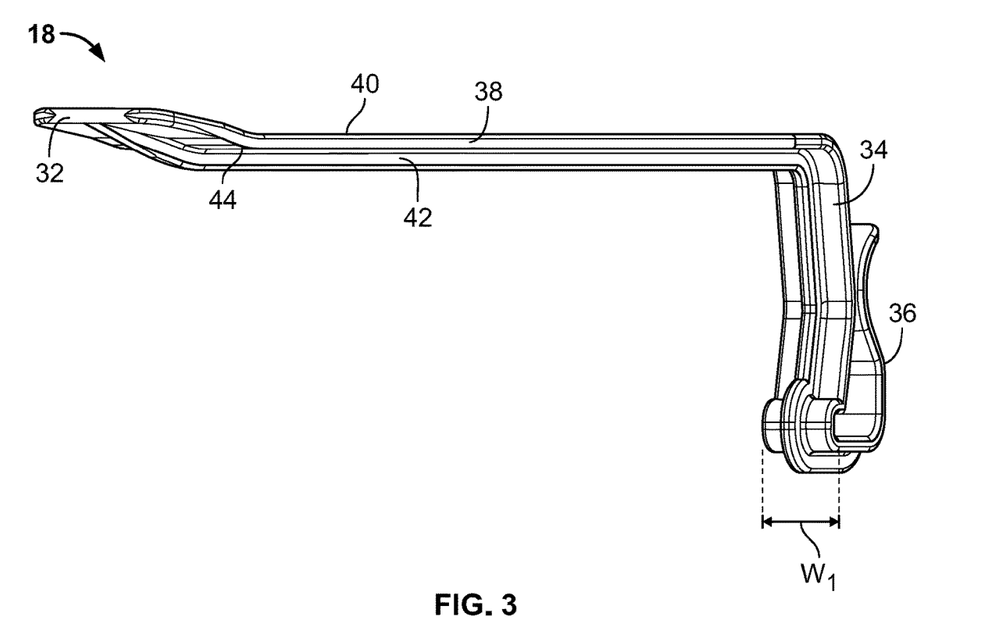
FIG. 3 is a perspective view of a rod of the product bag retention assembly of FIG. 1.
Figure 4:
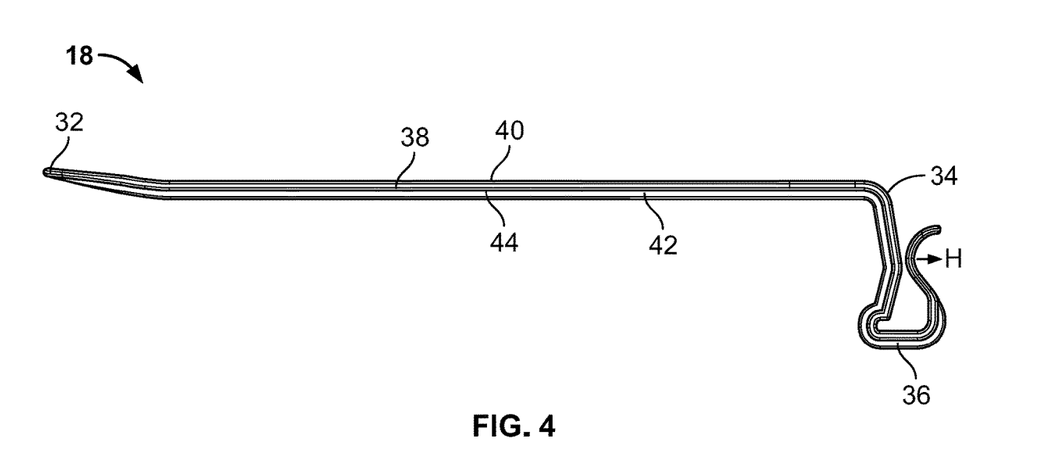
FIG. 4 is a side view of the rod of FIG. 3.

As shown in FIGS. 3 and 4, the rod 18 includes a first end 32, a second end 34 defining a hook 36, and a body 38 extending between the first end 32 and the second end 34. The body 38 of the rod 18 is generally flat and relatively thin to discreetly fit between two horizontal surfaces of a piece of furniture without noticeably affecting the comfort or feel of the furniture. The first end 32 is slightly bent upward to provide resistance to the rod 18 so that the rod 18 does not pull out of the furniture when added weight of fluid is in the bag 12. In another example, the first end 32 of the rod 18 may be ribbed to provide added resistance and to frictionally engage the rod 18 with the horizontal surfaces of the piece of furniture. The body 38 has a flat first surface 40, and a spine 42 extending from a second surface 44. The spine 42 is a centrally-located ridge protruding from the second surface 44 and extends at least partially along the body 38 of the rod 18 for added structural support and to provide rigidity such that the rod 18 cantilevers a suspended product bag 12 without snapping or permanently deforming. The second end 34 of the rod 18 is bent downwardly and away from the flat portion of the body 38 at substantially a right angle before curving to form the hook 36. The hook 36 curves outwardly (i.e., away from the first end 32) to flexibly receive the handle 22 of the assembly 10. However, in another example, the hook 36 may be shaped differently and may instead curve inwardly toward the first end 32 of the rod 18. In other examples, the hook 36 may instead be a loop, clasp, or other structure that securely receives the handle 22 defined by the holes 28A, 28B extending through the wall 29 of the bag 24. In yet another example, the product bag 12 may hang directly from the hook 36 without the use of the security bag 24.

In this example, the hook 36 is configured to slightly deform by opening in a direction H to receive the handle 22 before returning to its initially closed configuration. The handle 22 engages the hook 36 by forcing the hook 36 to open in the H direction before the hook returns to its initial configuration. After returning back to its initial configuration, the hook 36 securely retains the handle 22 to the rod 18. In the illustrated example, the hook 36 has a width W1 that is sized to fit in a notch 46 (FIG. 2) formed in the handle 22 such that the hook 36 securely fits into the notch 46 and keeps the handle 22 from sliding relative to the hook 36. The hook 36 may couple to the handle 22 by a snap-fit connection, and more particularly, the hook 36 may snap-fit into the notch 46 of the handle 22. To remove the handle 22 from the rod 18, the hook 36 is held relative to the handle 22 while the handle 22 is lifted upwardly and out of the hook 36. The hook 36 flexibly bends once more to remove the handle 22 from the rod 18.

In the illustrated example, the support brace 18 is a rod that may be a flexible or rigid material. However, in other examples, the support brace 18 may be a belt or a strap made of a woven or flexible material such as, for example, fabric, polymer, metal, or a combination of materials. In the example of a belt, the support brace 18 would include a locking component, such as a buckle, that would secure the belt around the piece of furniture such that a portion of the belt would protrude from the piece of furniture to removably couple to the product bag 12.

Figure 5:
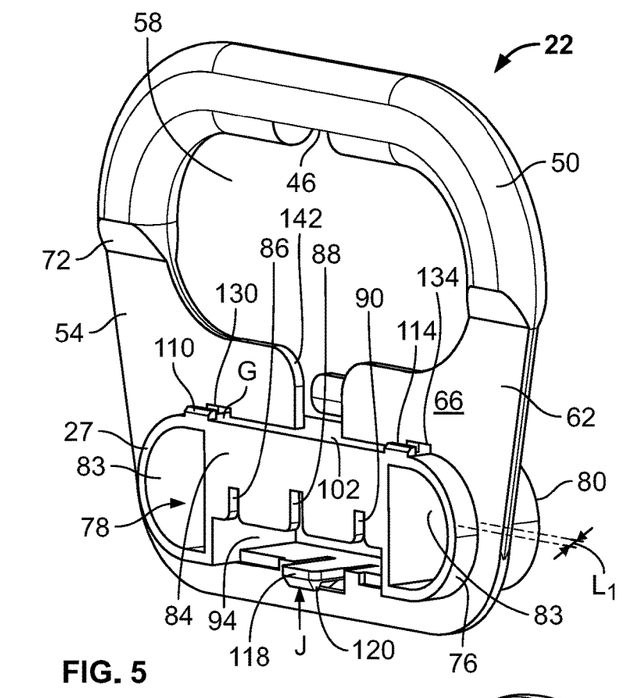
FIG. 5 is a front perspective view of a handle of the product bag retention assembly of FIG. 1.
Figure 6:
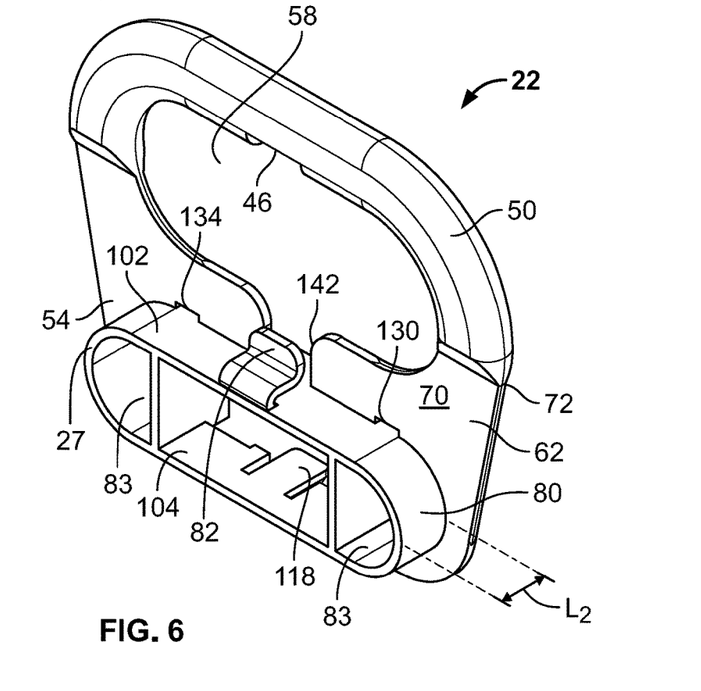
FIG. 6 is a back perspective view of the handle of FIG. 5.
Figure 7:
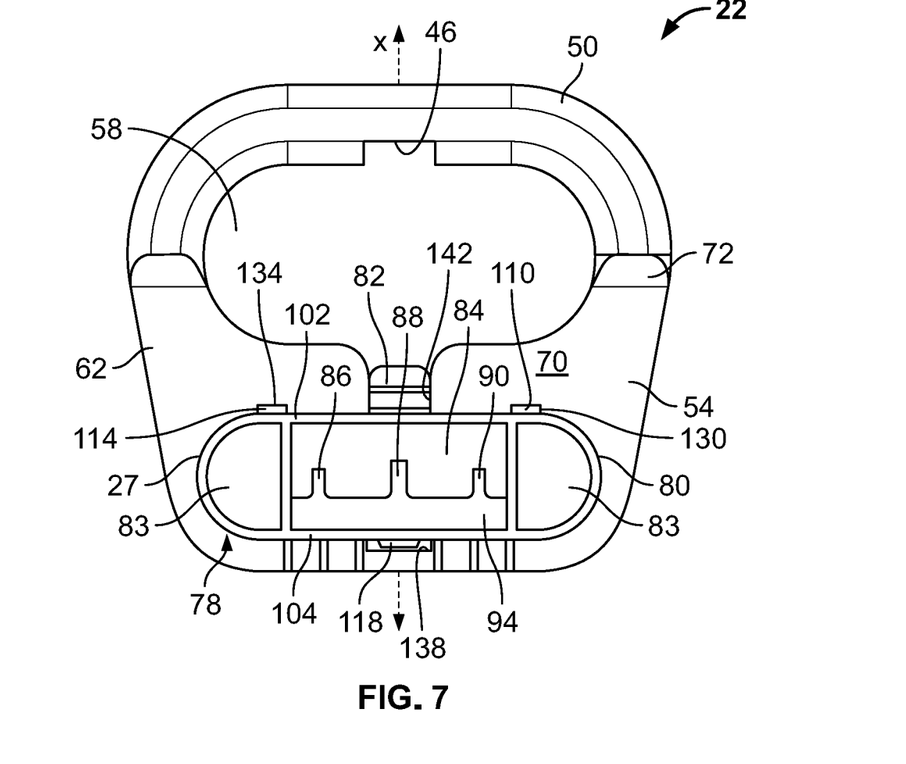
FIG. 7 is a back view of the handle of FIG. 5.

The handle 22, which is more clearly shown in FIGS. 5-7, includes a grip portion 50 and a support portion 54 extending from the grip portion 50. The grip portion 50 is shaped for a user to comfortably hold the handle 22 and defines an opening 58. The opening 58 is sized to receive a person's hand and also to receive the hook 36 to couple the hook 36 to the handle 22. As mentioned previously, the notch 46 of the handle 22 is sized to receive the hook 36 of the rod 18. As shown more clearly in FIGS. 5-7, the notch 46 is formed in the grip portion 50 and is adjacent to the opening 58 of the handle 22. The support portion 54 includes a base plate 62 stepped inwardly relative to the grip portion 54 of the handle 22 and includes a first surface 66 (FIG. 5) and a second surface 70 (FIGS. 6 and 7). In the illustrated example, the grip portion 50 provides a curved grip with a tubular body, and the base plate 62 is flat by comparison. The grip portion 50 meets the support portion 54 at a seam 72, which is sloped to smoothly integrate the rounded grip portion 50 with the flat base plate 62 of the handle 22. The seam 72 may align with an opening of the bag 24, as shown in FIG. 1. In the illustrated example, the grip portion 50 and the support portion 54 are integrally formed, however, in other examples, the grip portion 50 and the support portion 54 may be separate components that are securely coupled by fasteners, welding, adhesive, or other suitable methods.

In FIGS. 5-7, the handle 22 includes the platform 27 that is operatively coupled to the support portion 54, and is configured to receive and support a mounting device (e.g., mounting arms 26) of a product bag 12. The platform 27 couples to the security bag 24 by extending through one of the holes 28A, 28B (e.g., defining handles) formed in the wall 29 of the bag 24. As shown in FIG. 5, a first portion 76 of the platform 27 extends away from the first surface 66 of the base plate 62 a length L1. The platform 27 includes an aperture arrangement 78 including various apertures sized and shaped to receive a variety of different mounting devices of product bags 12 commonly used in the medical industry. In FIG. 6, a second portion 80 of the platform 27 extends away from the second surface 70 of the base plate 72 a length L2. The length L2 of the second portion 80 is greater than the length L1 of the first portion 76, however, in other examples, the platform 27 may extend equally away from either surface 66, 70 of the base plate 62.

Adjacent a distal edge of the platform 27, a hook 82 curves upwardly and inwardly toward the base plate 62 before curving in a perpendicular direction relative to the platform 27. The hook 82 is configured to retain a top edge of the second hole 28B of the bag 24 (e.g., the handle of the bag 24). The hook 82 is formed in the second portion 80 of the platform 27. In this way, the hook 82 is configured to partially close the security bag 24 around the handle 22 and the product bag 12 when the first portion 76 of the platform 27 is secured to the security bag 24. Even when the hook 82 retains a portion of the security bag 24, the security bag 24 remains open to permit the tube 14 to extend outside of the bag 24 and connect to the patient (e.g., via an ostomy bag). The platform 27 is shaped to extend through at least one hole 28A, 28B formed in the bag 24 such that the support portion 54 of the handle 22 is disposed within the bag 24 and the grip portion 50 is outside of the bag 24, as shown in FIG. 1. In the illustrated example, the first portion 76 of the platform 27 protrudes through the first hole 28A in the bag 24, and the second portion 80 of the platform 27 is configured to protrude through the second hole 28B in the bag 24. In another example, the safety bag 24 may be secured directly to the rod 18 rather than directly coupled to the platform 27. For example, the safety bag 24 may include a drawstring, adhesive, or other fastening device that permits a user to cinch the bag 24 around the rod 18 without securing the bag 24 to the platform 27.

Turning back to FIGS. 5-7, the aperture arrangement 78 of the platform 27 includes a plurality of apertures to receive different mounting devices of various product bags 12. The aperture arrangement 78 of the platform 27 includes first and second semi-circular apertures 83, and a guide plate 84 defining first, second, and third vertical slots 86, 88, and 90, and a horizontal rectangular opening 94 disposed beneath and connected to the vertical slots 86, 88, 90. The guide plate 84 is disposed at an outer edge of the first portion 76 and extends in a perpendicular direction relative to the length L1 of the platform 27. As more clearly shown in FIG. 7, the first, second, and third slots 86, 88, and 90 formed in the guide plate 84 are different sizes. In particular, the first and third slots 86 and 90 are identical and evenly spaced from the second vertical slot 88, which is centrally located relative to the handle 22. The second slot 88 is also slightly wider in both vertical and horizontal directions (in FIG. 7). In this case, the handle 22 is symmetrical about a centerline axis X, and the second vertical slot 88 is parallel relative to the axis X. As shown in the illustrated example of FIGS. 1 and 2, the first and second semi-circular apertures 83 are configured to receive the mounting arms 26 of the product bag 12. However, the platform 27 of the illustrated example is also configured to receive mounting devices (e.g., strings, hooks, ties, rings) of a number of different product bags manufactured by, for example, Rusch, Medline, Dover, Hollister, Bard, and Coveen. Additionally, the aperture arrangement 78 may be configured differently in other examples, and may include more or less apertures than what is illustrated. In one example, the guide plate 84 may be removably attached to the base plate 62 such that the platform 27 can be adaptable to a particular product bag manufacturer. In yet another example, the product bag 12 may be directly attached to the rod 18 instead mounting to the platform 27.

Figure 8:
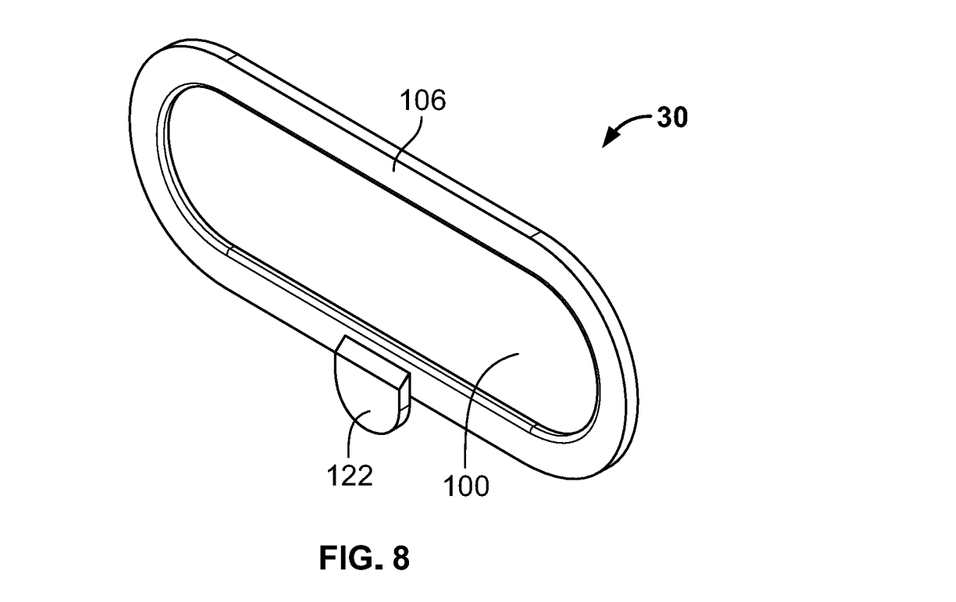
FIG. 8 is a perspective view of a ring of the product bag retention assembly of FIG. 1.

The platform 27 of the handle 22 is removably coupled to the bag 24 by securing the ring 30 of FIG. 8 around an outer perimeter of the platform 27 and clamping a portion of the security bag 24 between the ring 30 and the handle 22. As shown in FIGS. 5-8, the platform 27 has an oval-shaped perimeter to match an oval opening 100 of the ring 30, and engages with an upper ledge 102 and a lower ledge 104 of the platform 27. In particular, the upper ledge 102 of the first portion 76 of the platform 27 includes first and second pegs 110, 114 that engage a linear portion 106 of the ring 30. The pegs 110, 114 protrude from the ledge 102 of the platform 27 to securably engage the ring 30 between the pegs 110, 114 and the first surface 66 of the base plate 62. In particular, the pegs 110, 114 are spaced away from the first surface 66 of the base plate 62 by a gap G that is sized to receive the linear portion 106 of the ring 30. Once the ring 30 is disposed in the gap G, the ring 30 may be pushed downward and toward the platform 27 to engage a flexible latch 118. The latch 118 has an angled end 120 and is formed in the lower ledge 104 the platform 27, and therefore is disposed below the upper ledge 102. In this example, the latch 118 is configured to slightly deform (e.g., flex, bend, deflect) upward in a direction J before returning to its original, unbiased position. By returning back to its initial position, the latch 118 securely retains the ring 30 to the platform 27 and the angled end 120 engages the ring 30.

To operatively couple the ring 30 to the platform 27, the linear portion 106 of the ring 30 is inserted into the gap G defined between the platform 27 and the base plate 62, and a tab 122 of the ring 30 is pivoted downward and inward relative to the platform 27 until the ring 30 engages the latch 118 of the platform 27. During engagement, the ring 30 pushes the latch 118 upward (in the J direction) until the angled end 120 of the latch 118 snaps against the ring 30. To remove the ring 30 from the platform 27, the latch 118 may be pushed upward in the J direction to disengage the ring 30 from the platform 27, and a user may pull the tab 122 away from the latch 118. It will be appreciated that the ring 30 and the platform 27 may removably couple by other coupling methods. In the illustrated example, the pegs 110, 114 are positioned above and on either side of the guide plate 84, however, in other examples, the platform 27 may include one peg or more than two pegs protruding from different locations around the perimeter of the platform 27.

The platform 27 may be a separate component from the handle 22 such that the platform 27 is disposed within a cut-out (e.g., aperture, opening) formed in the base plate 62. The cut-out may be sized and shaped to receive the oval perimeter of the platform 27, the first and second pegs 110, 114, the deflecting latch 118, and the hook 82 when sliding the platform 27 into the cut-out of the base plate 62. For example, as shown in FIG. 7, the base plate 62 includes first and second cut-outs 130, 134 that are shaped to receive the first and second pegs 110, 114, a third cut-out 138 that is shaped to receive the latch 118 and to permit the latch 118 to deflect in the J direction, and a fourth cut-out 142 that is shaped to receive the hook 82 of the platform 27. In this example, the platform 27 is inserted through the cut-out of the base plate 62 until the length L1 of the first portion 76 extends from the first surface 66 of the base plate 62. In the illustrated example, the ring 30 and the platform 27 are oval to facilitate coupling the ring 30 to the platform 27. However, in other examples, the platform 27 and the ring 30 may have a different geometry and shape, such as, for example, rectangular, circular, or polygonal.

Figure 9:
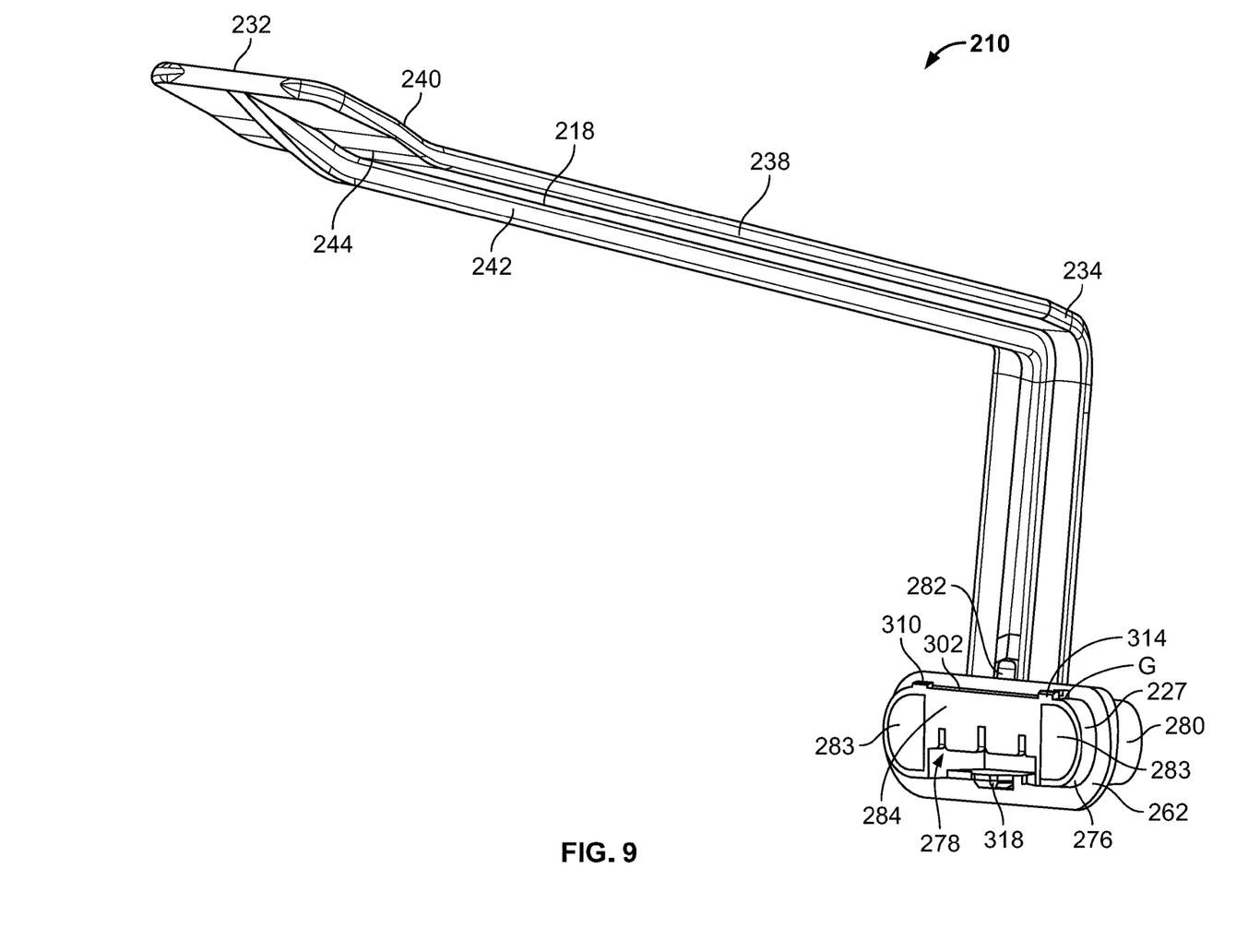
FIG. 9 is a perspective view of a second exemplary product bag retention assembly in accordance with the teachings of the present disclosure.

Turning now to FIG. 9, a second exemplary product bag retention assembly 210 is constructed according to the teachings of the present disclosure. The second exemplary product bag retention assembly 210 includes a second exemplary rod 218 and a second exemplary platform 227 that may be used with the security bag 24 and product bag 12 of FIGS. 1 and 2 to suspend the product bag 12 from a piece of furniture in an upright position. The second exemplary rod 218 and second exemplary platform 227 are similar to the rod 18 and platform 27, respectively, of the first exemplary product bag retention assembly 10 of FIGS. 1-7. Thus, for ease of reference, and to the extent possible, the same or similar components of the second exemplary rod 218 will retain the same reference numbers as outlined above with respect to the first exemplary rod 18 although the reference numbers will be increased by 200. Likewise, the same or similar components of the second exemplary platform 227 will retain the same reference numbers as outlined above with respect to the first exemplary platform 27, although the reference numbers will be increased by 200. However, the second exemplary rod 218 and the second exemplary platform 227 differ from the first exemplary rod 18 and first exemplary platform 27, respectively, in the manner discussed below.

Similar to the first exemplary rod 18, the second exemplary rod 218 includes a first end 232 that is configured to engage with a piece of furniture and a second end 234 that is operatively coupled to the platform 227. However, the rod 218 differs from the first exemplary rod 18 as the second exemplary rod 218 does not provide a hook 36. Instead, the second end 234 of the rod 218 is fastened to the platform 227 such that a mounting device 26 of a product bag 12 may be directly mounted to the rod 218 via the platform 227. In one example, the second end 234 of the rod 218 is integrally formed with the platform 227. Similar to the first exemplary platform 27 of FIGS. 1-7, the second exemplary platform 227 is arranged to clamp a portion of the security bag 24 between the platform 227 and the ring 30 when the ring 30 is coupled to first and second pegs 310, 314 and a latch 318 of the platform 227. The platform 227 of FIG. 9 includes a flange 262, which surrounds the oval-shaped perimeter of the platform 227 and also serves to separate a first portion 276 of the platform 227 from a second portion 280 of the platform 227.

In further accordance with any one or more of the foregoing first and second exemplary product bag retention assemblies 10, 210, a method of assembling and suspending a product bag 12 from a piece of furniture generally includes the steps of providing the rod 18, 218 in which the second end 34, 234 is operatively coupled to the platform 27, 227 for receiving a mounting device 26 of the product bag 12, and disposing the first end 32, 232 of the rod 18, 218 between a first surface and a second surface of a piece of furniture such that the second end 34, 234 of the rod 18, 218 is spaced away from the piece of furniture. For example, the first end 32, 232 of the rod 18, 218 may be inserted between a box spring and a mattress of a typical bed to suspend the product bag 12 from the bed. In another example, the first end 32, 232 of the rod 18, 218 may be inserted between a chair or couch frame and a cushion.

Typically, the product bag 12 is coupled to the platform 27, 227 before inserting the rod 18, 218 into the piece of furniture. The product bag 12 is coupled to the platform 27, 227 such that the product bag 12 is suspended outwardly and away from the piece of furniture and hangs from the platform 27, 227 in an upright position. The product bag 12 may be coupled to the platform 27, 227 by sliding the mounting device 26 of the product bag 12 through an aperture (e.g., the aperture arrangements 78, 278) formed in the platform 27, 227. The security bag 24 is coupled to the platform 27, 227 by disposing the first portion 76, 276 of the platform 27, 227 through the hole 28A in the bag 24. The ring 30 is securely attached to the platform 27, 227 such that a portion of the security bag 24 is clamped between the ring 30 and the platform 27, 227. In some cases, the bag 24 may be attached to the platform 27, 227 prior to mounting the product bag 12 to the platform 27, 227. To replace the bag 24, the method includes removing the ring 30 from the platform 27, 227 and removing the security bag 24 from the platform 27, 227. A second security bag 24 is then coupled to the platform 27, 227 by disposing a portion of the platform 27, 227 through a hole 28A in the second bag 24. The ring 30 may again be secured to the platform 27, 227 to clamp a portion of the second bag 24 between the ring 30 and the platform 27, 227.

With regards to FIGS. 1 and 2, the platform 27 is coupled to the support portion 54 of the handle 22 of the first exemplary product bag retention assembly 10. In this example, the handle 22 is coupled to the hook 36 of the rod 18 by engaging the handle 22 with the hook 36. In one example, the handle 22 couples to the hook 36 by snap-fitting the hook 36 into the notch 46 formed the handle 22. The product bag 12 can be mounted to the handle 22 before or after disposing the product bag 12 into the bag 24. Once the product bag 12 is disposed in the bag 24, the ring 30 may securably coupled to the handle 22, thereby clamping the bag 24 between the handle 22 and the ring 30. The handle 22 is removable from the disposable bag 24 by removing the ring 30 and attaching the handle 22 of a different plastic bag 24. By removing the handle 22 from the hook 36 of the rod 18, the patient may carry the product bag 12 to the bathroom to empty and rinse the product bag 12 before using the product bag 12 again. The rod 18 remains attached to the piece of furniture so that the patient can easily connect the handle 22 to the hook 36 for use.

The first and second exemplary product bag retention assemblies 10, 210 may provide a patient with confidence that their connected medical product bag is safely secured and out of the way while the patient rests. As described herein, the product bag retention assembly 10, 210 safeguards against accidental leaks of the connected product bag 12 while the patient is asleep. In case the product bag 12 were to leak, the security bag 24 guards against any spilling on the floor or furniture. The patient can easily disassemble the assembly 10, 210, discard or wash the removable disposable bag 24, and replace the security bag 24 with a new bag 24 or a clean bag 24. The rod 18, 218 may be lightweight and easy to use such that a patient can travel with it and use it with a variety of different pieces of furniture. The slim body 38, 238 of the rod 18, 218 permits a patient to slip the assembly 10, 210 between two horizontal surfaces without worrying that the product bag 12 will fall, turn-over, or become detached while the patient sleeps. The design of the assembly 10, 210 is compact such the patient can place the security bag 24 flat against a bed, discreetly hidden from view. Further, the flexible coupling mechanisms (e.g., the hook 36 and handle 22, the platform 27, 227 and the ring 30) facilitate easy assembly and disassembly of the product bag 12 from the handle 22 and/or from the rod 18, 218.

The different components of the assemblies 10, 210 are preferably made of a durable plastic, such as polyethylene, that may be formed by injection molding, thermoforming, or compression molding, but may instead be formed of any other suitable and durable material including metal, fiberglass, or other similar materials, or any combination of these materials. In other examples, the components of the assemblies 10, 210 may be made using an additive manufacturing (AM) technique or process that builds three-dimensional objects by adding successive layers of material on a material or receiving surface. The AM technique may be performed by any suitable machine or combination of machines. The AM technique may typically involve or use a computer, three-dimensional modeling software (e.g., Computer Aided Design, or CAD, software), machine equipment, and layering material. Once a CAD model is produced, the machine equipment may read in data from the CAD file and layer or add successive layers of liquid, powder, sheet material (for example) in a layer-upon-layer fashion to fabricate a three-dimensional object. The AM technique may include any of several techniques or processes, such as, for example, a stereolithography ("SLA") process, digital light processing ("DLP"), a fused deposition modeling ("FDM") process, a multi-jet modeling ("MJM") process, a selective laser sintering ("SLS") process, a selective laser melting ("SLM") process, an electronic beam melting ("EBM") process, and an arc welding AM process. In some embodiments, the AM process may include a directed energy laser deposition process. Such a directed energy laser deposition process may be performed by a multi-axis computer-numerically-controlled ("CNC") lathe with directed energy laser deposition capabilities. Other manufacturing techniques may be utilized to create the assemblies 10, 210 according to the present disclosure, and are not limited to the techniques herein.

The figures and description provided herein depict and describe preferred embodiments of product bag retention assembly for purposes of illustration only. One skilled in the art will readily recognize from the foregoing discussion that alternative embodiments of the components illustrated herein may be employed without departing from the principles described herein. Thus, upon reading this disclosure, those of skill in the art will appreciate still additional alternative structural and functional designs for the product bag retention assembly. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the methods and components disclosed herein without departing from the spirit and scope defined in the appended claims.

What is claimed:

1. A product bag retention assembly, the assembly comprising:
    a support brace having a first end and a second end defining a hook;
    a handle including a grip portion and a support portion extending from the grip portion, the grip portion removably coupled to the hook of the support brace, the support portion having a first surface and a second surface,
    a platform operatively coupled to the support portion of the handle and extending away from the first surface of the support portion, the platform defining an aperture sized to receive a mounting device of a product bag;
    a bag including a wall defining a chamber to receive the product bag, the bag including a hole formed in the wall and sized to receive the platform; and
    a ring removably coupled to the platform;
    wherein a portion of the bag is clamped between the ring and the handle when the platform is disposed through the hole of the bag and the ring is coupled to the platform, and
    wherein the platform further defines a plurality of apertures arranged to receive and support a mounting device of a product bag.

2. The product bag retention assembly of claim 1, wherein the platform is integrally formed with the handle.

3. The product bag retention assembly of claim 1, wherein when the hook is coupled to the grip portion of the handle, the grip portion is received in a gap defined by the hook.

4. The product bag retention assembly of claim 1, further comprising a latch formed in the platform and configured to elastically deform to allow the ring to snap fit to the platform.

5. The product bag retention assembly of claim 1, further comprising a notch formed in the grip portion of the handle, the notch sized to receive the hook of the support brace; and wherein the handle is coupled to the hook of the support brace by a snap-fit connection.

6. The product bag retention assembly of claim 1, wherein the platform includes a hook adjacent to the second surface of the support portion, the hook of the platform removably coupled to a second hole of the bag.

7. The assembly of claim 1, wherein when the platform is disposed through the hole of the bag, the support portion of the handle is disposed in the chamber of the bag.

8. The assembly of claim 1, wherein the platform includes a ledge having a planar surface that is perpendicular relative to the first surface of the support portion.

9. A method for suspending a product bag from a piece of furniture, the method comprising:
    providing the product bag retention assembly of claim 1;
    providing a rod having a first end, a second end, and a body extending between the first end and the second end, the second end operatively coupled to a platform for receiving a mounting device of a product bag;
    disposing the first end of the rod between a first surface and a second surface of a piece of furniture such that the second end of the rod is spaced away from the piece of furniture;
    coupling a product bag to the platform such that the product bag is suspended outwardly and away from the piece of furniture, the product bag hanging from the platform in an upright position.

10. The method of claim 9, wherein coupling a product bag to the platform includes sliding a mounting device of the product bag through an aperture formed in the platform.

11. The method of claim 9, further comprising coupling a handle to a hook formed in the second end of the rod, the handle including a grip portion, a support portion extending from the grip portion, and wherein the platform extends outwardly from the support portion of the handle.

12. The method of claim 9, further comprising coupling a bag to the platform by disposing a portion of the platform through a hole in the bag, the bag including a wall defining a chamber sized to receive the product bag, wherein the hole is formed in the wall of the bag; and securably attaching a ring to the platform such that a portion of the bag is clamped between the ring and the platform.

13. The method of claim 12, further comprising coupling a second bag to the platform by disposing a portion of the platform through a hole in the second bag.

* * * * *